United States Patent
Stefanchik et al.

(10) Patent No.: US 8,211,143 B2
(45) Date of Patent: Jul. 3, 2012

(54) SUTURING DEVICE

(76) Inventors: David Stefanchik, Morrow, OH (US);
James A. Craft, Lexington, KY (US)

(*) Notice: Subject to any disclaimer, the term of this patent is extended or adjusted under 35 U.S.C. 154(b) by 1021 days.

(21) Appl. No.: 11/095,439

(22) Filed: Mar. 31, 2005

(65) Prior Publication Data
US 2006/0224184 A1 Oct. 5, 2006

(51) Int. Cl.
*A61B 17/06* (2006.01)
(52) U.S. Cl. .................................................... 606/223
(58) Field of Classification Search .......... 606/222–227, 606/144; 112/222–227; 163/4–5
See application file for complete search history.

(56) References Cited

U.S. PATENT DOCUMENTS

| | | | |
|---|---|---|---|
| 3,910,281 A | 10/1975 | Kletschka et al. | |
| 4,345,601 A * | 8/1982 | Fukuda | 606/147 |
| 5,350,385 A | 9/1994 | Christy | |
| 5,571,119 A | 11/1996 | Atala | |
| 5,653,717 A | 8/1997 | Ko et al. | |
| 5,919,199 A | 7/1999 | Mers Kelly et al. | |
| 5,935,138 A | 8/1999 | McJames, II et al. | |
| 6,015,428 A * | 1/2000 | Pagedas | 606/232 |
| 6,283,979 B1 * | 9/2001 | Mers Kelly et al. | 606/139 |
| 6,454,778 B2 | 9/2002 | Kortenbach | |
| 6,923,819 B2 * | 8/2005 | Meade et al. | 606/144 |
| 7,125,413 B2 * | 10/2006 | Grigoryants et al. | 606/153 |
| 2003/0083674 A1 * | 5/2003 | Gibbens, III | 606/144 |
| 2003/0083695 A1 | 5/2003 | Morris et al. | |
| 2003/0233108 A1 * | 12/2003 | Gellman et al. | 606/144 |
| 2004/0186515 A1 | 9/2004 | Rosenblatt | |

FOREIGN PATENT DOCUMENTS
FR 2746292 9/1997

OTHER PUBLICATIONS
International Search Report dated Jan. 27, 2010; International Application No. 08075604.2.

* cited by examiner

*Primary Examiner* — Gary Jackson
*Assistant Examiner* — Eric Blatt
(74) *Attorney, Agent, or Firm* — Dean L. Garner (57) ABSTRACT

A medical apparatus and method useful for suturing tissue is disclosed. The medical apparatus can include a curved needle and an apparatus suitable for providing endoscopic suturing. The apparatus can include a needle drive for driving the curved needle about a generally arcuate path. The curved needle can be deformed to form a closed needle structure.

19 Claims, 13 Drawing Sheets

SUTURING DEVICE

FIELD OF THE INVENTION

The present invention is related generally to medical devices and more particularly to devices useful in endoscopic suturing.

BACKGROUND OF THE INVENTION

The use of needle and suture in closing tissue defects or otherwise fastening tissue is known in the art. For instance, U.S. Pat. No. 3,910,281 discloses a suture anchor which can be used with a needle and suture material. It is also known to employ suture methods in endoscopic applications. For instance, U.S. Pat. No. 6,454,778 discloses a surgical instrument for applying sutures to tissue, which includes a needle deployment mechanism.

Still, scientists and engineers continue to seek improved devices and methods for securing tissue, including devices and methods which can be used endoscopically and/or in open procedures.

SUMMARY OF THE INVENTION

In one embodiment, the present invention provides a needle for use in suturing. The needle has a generally arcuate, C-shaped configuration extending through an arc of at least about 180 degrees, and the needle is deformable from a first configuration, such as an open C shape, to a second configuration, such a closed configuration.

In another embodiment, a method of suturing is provided. The method comprises providing a needle deformable from a first configuration (such as an open configuration) to a second configuration (such as a closed configuration); providing suture material associated with the needle; passing the needle at least one time through tissue; and deforming the needle from the first configuration to the second configuration.

In another embodiment, the invention provides a needle drive assembly for receiving a generally arcuate needle and driving the needle along a generally arcuate path. The drive assembly can provide 360° motion of the C-shaped suturing needle within a curved, generally arcuate guide track so that multiple suturing passes may be made, without oscillatory motion, wherein the needle is driven by two more toothed sprockets. The drive assembly can provide one-handed operation, which frees the operator's other hand for tissue manipulation. The drive assembly includes an element, such as a slidable plunger, for deforming the needle. In one embodiment, once the needle is closed upon itself, the smaller shape of the closed needle enables the needle to be discharged from the drive assembly so that the needle may remain attached to the suturing material at the first end and serve as an anchor at the first end thereof.

The present invention provides an apparatus and method useful for suturing body tissue. In one embodiment the invention provides a suturing mechanism as an end-effector removably attachable to an inserted end of a flexible endoscope for use within a patient's alimentary canal to stop bleeding, to close a wound, or any of numerous surgical applications for suture, well known in the art, without having to surgically enter the body cavity.

DETAILED DESCRIPTION

FIGS. 1-4 illustrate one embodiment of a suturing mechanism according to the present invention. In one embodiment, suturing mechanism 2 can include a housing 4, a drive sprocket 30, a driven sprocket 40, a drive belt 50, a flexible drive cable 60, a needle 70 (which may be a malleable, arcuate, generally C-shaped needle), a suturing material 100, a slidable suture material anchor 110, a pull cable 118, and a plunger 120.

Figure 1:
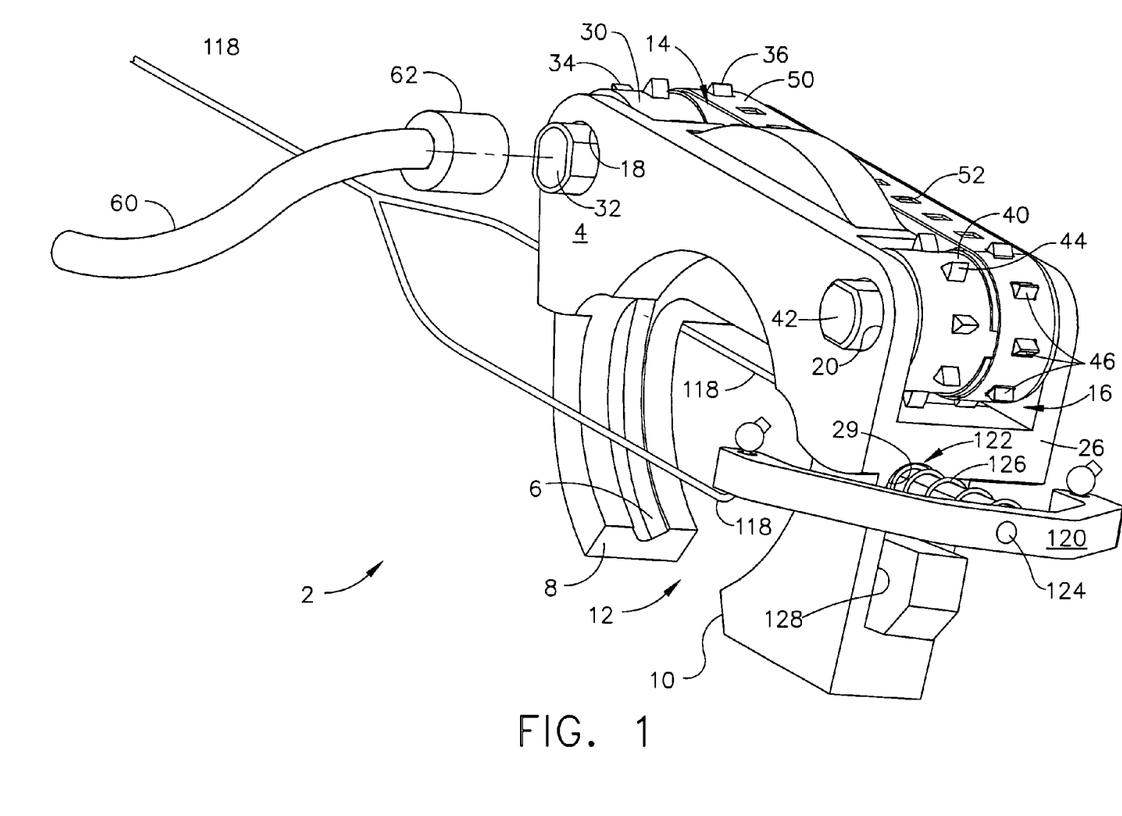
FIG. 1 is a perspective view of a suturing mechanism showing a housing, generally circular needle track and drive train.

As shown in FIG. 1, housing 4 can have an arcuate groove therein, forming a needle track 6. Track 6 can be sized to hold C-shaped needle 70 shown in FIGS. 2-3. Track 6 can have an open V-shape, U-shape, rectangular, trapezoidal, or other suitable shape, and track 6 can extend circumferentially about a portion of needle 70. In one embodiment, track 6 can extend circumferentially about needle 70 through an angle of no more than about 180 degrees. Housing 4 can have a first surface 8 and a second surface 10 which define an open end 12 in track 6 providing clearance between surface 8 and surface 10. Housing 4 can be made of series 300 stainless steel via machining processes commonly known in the fabrication art, such as casting, turning, milling, and electro-discharge machining (EDM). Alternatively, housing 4 can be formed of another suitable biocompatible materials, including metallic and non-metallic biocompatible materials. Housing 4 can be about 0.74 inches long, about 0.25 inches wide, and about 0.55 inches high. Needle track 6 is can be about 0.50 inches in diameter at its root and can have a groove depth of about 0.016 inches. Open end 12 can be about 0.25 inches wide.

Housing 4 can also have a first slot 14 and a second slot 16 for housing drive sprocket 30 and driven sprocket 40 (sprockets 30 and 40 can be the same size or different sizes), respectively, and drive belt 50. Sprocket 30 can be associated with an axle 32, such as by axle 32 being splined and/or press-fit therethrough, and sprocket 40 can be associated with an axle 42, such as by being splined and/or press-fit therethrough. Axial clearance holes 18 and 20 can be formed in one or both sides of housing 4, and axles 32 and 42 can extend across slots 14 and 16, respectively. Axles 32 and 42 can be substantially parallel to each other.

Drive sprocket 30 has a first set of equally spaced teeth 34 and a second adjacent set of equally spaced teeth 36 extending about its circumference. Driven sprocket 40 has a first set of equally spaced teeth 44 and a second adjacent set of equally spaced teeth 46 extending about its circumference. Teeth 34 and 44 can have a common pitch. Teeth 36 and 46 can also have a common pitch, which may or may not be different from the pitch of teeth 34 and 44. Sprockets 30 and 40 may each be single unitary parts, or each of sprocket 30 and 40 can be formed of two components keyed together for ease of forming individual rows of teeth. Sprockets 30 and 40 can be made of series 300 stainless steel and teeth 34, 36, 44, and 46 can be formed by a wire EDM process. Each sprocket can be about 0.15 inches diameter at the root of the teeth. Axles 32 and 42 can be made of series 300 stainless steel and can be about 0.077 inches in diameter and about 0.325 inches long. Flats on each side of the axles 32 and 42 can be employed to define a spline shape or other non-circular shape which fits into similarly shaped non-circular holes in sprockets 30 and 40.

Drive belt 50 can be a continuous belt attached around sprockets 30 and 40. Drive belt 50 can employ apertures 52 equally spaced along the length thereof. Apertures 52 can have the same pitch as teeth 36 and 46 so that when drive sprocket 30 is rotated, drive belt 50 positively rotates driven sprocket 40 the same amount. Drive belt 50 can be made of any suitable biocompatible material, including without limitation a non-metallic material or a metallic material such as series 300 stainless steel. In one embodiment, the drive belt can have a thickness of about 0.002 inches, a width of about 0.072 inches, and a length of about 1.65 inches.

FIG. 1 shows twistable, flexible cable 60 positioned for cooperating with axle 32 of drive sprocket 30. Cable 60 can include a collar 62, which is removably attachable to axle 32 for assembly purposes, but is rotationally fixed thereto when assembled, such as by pin, spline or press-fit, so that when cable 60 rotates about its axis, axle 32 rotates, causing sprocket 30 to rotate, thereby driving belt 50 to rotate sprocket 40 in the same direction and speed as sprocket 30. Cable 60 can have a diameter of about 0.09 inches, and can be formed of any suitable material, including without limitation series 300 stainless steel wire similar to a speedometer cable, being relatively low in bending stiffness but relatively high in twisting stiffness. Lubrication of rotating and sliding parts in housing 4 can be accomplished with any suitable lubricant, including without limitation teflon coating, soap, or petroleum jelly.

Figure 2:
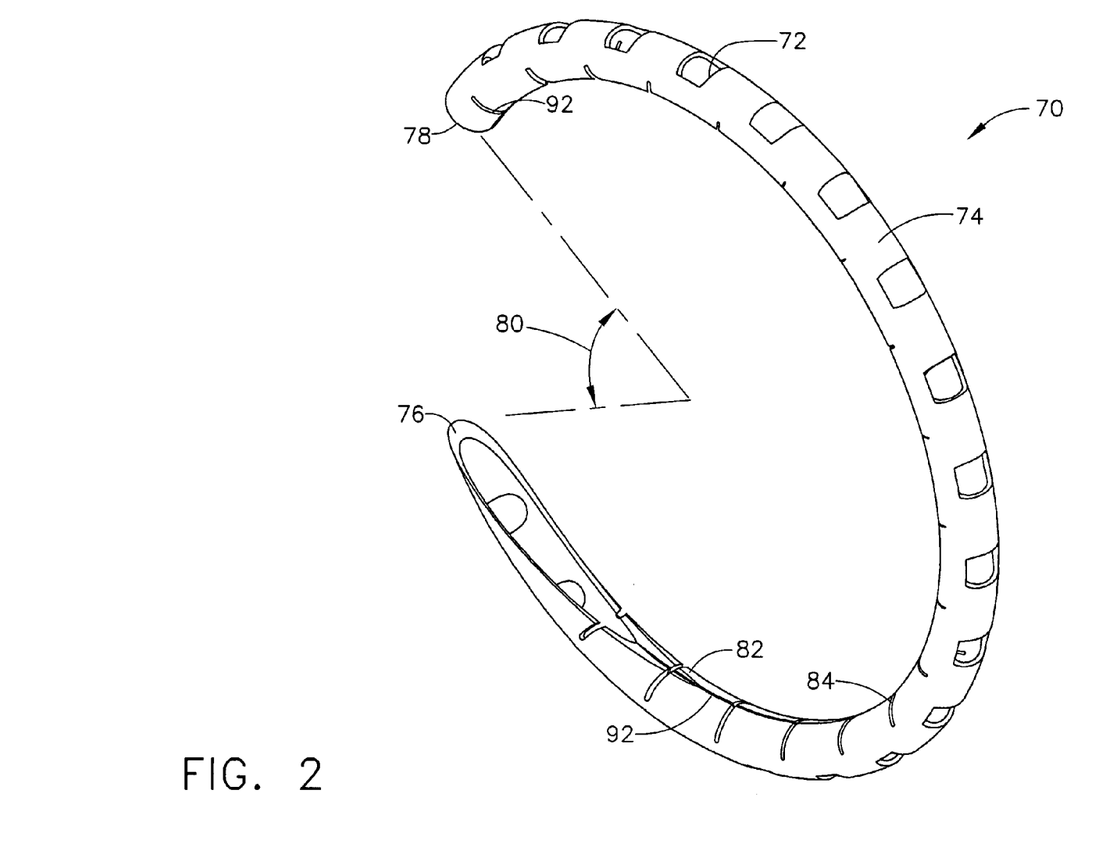
FIG. 2 is a perspective view of one embodiment of a C-shaped needle.
Figure 3:
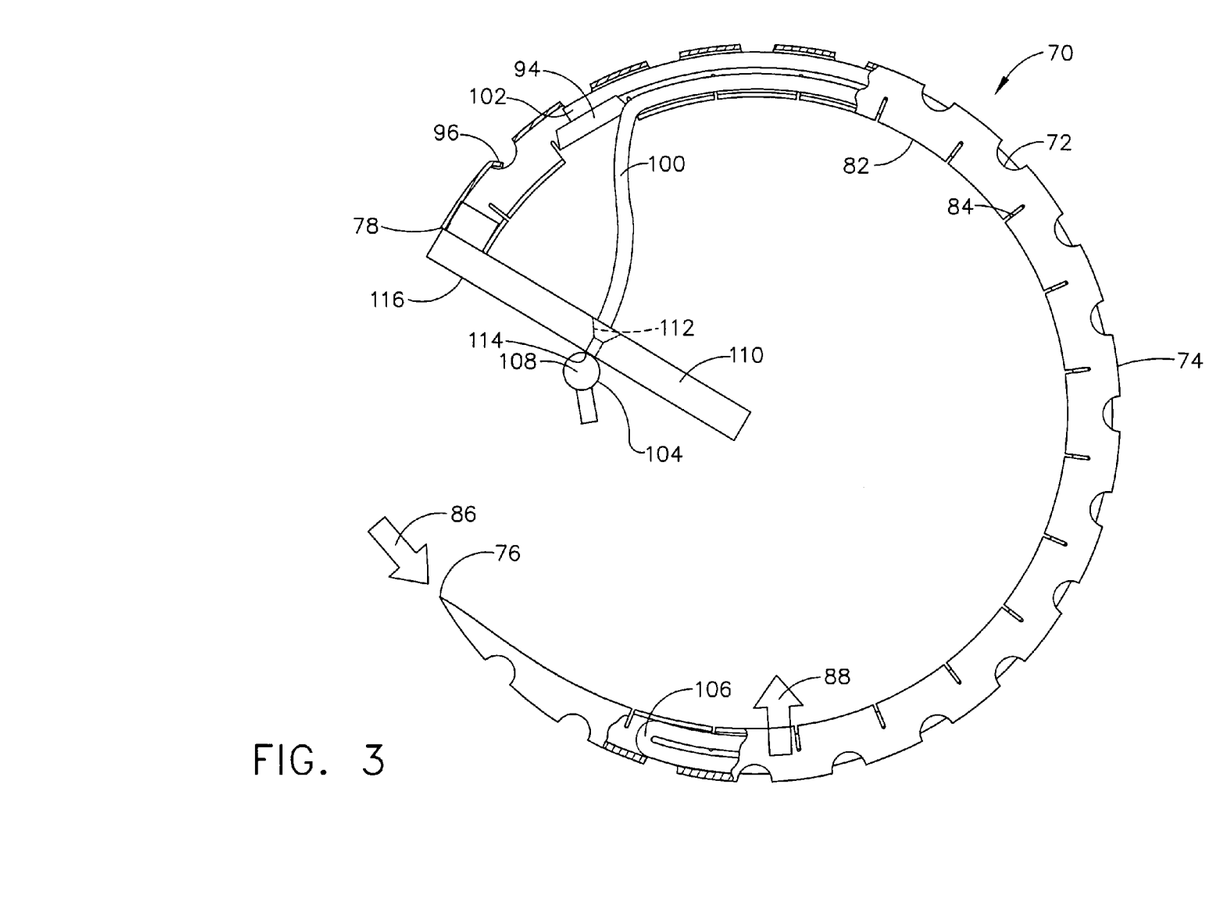
FIG. 3 is a side elevation view of the needle of FIG. 2, showing suturing material housed within the needle.
Figure 4:
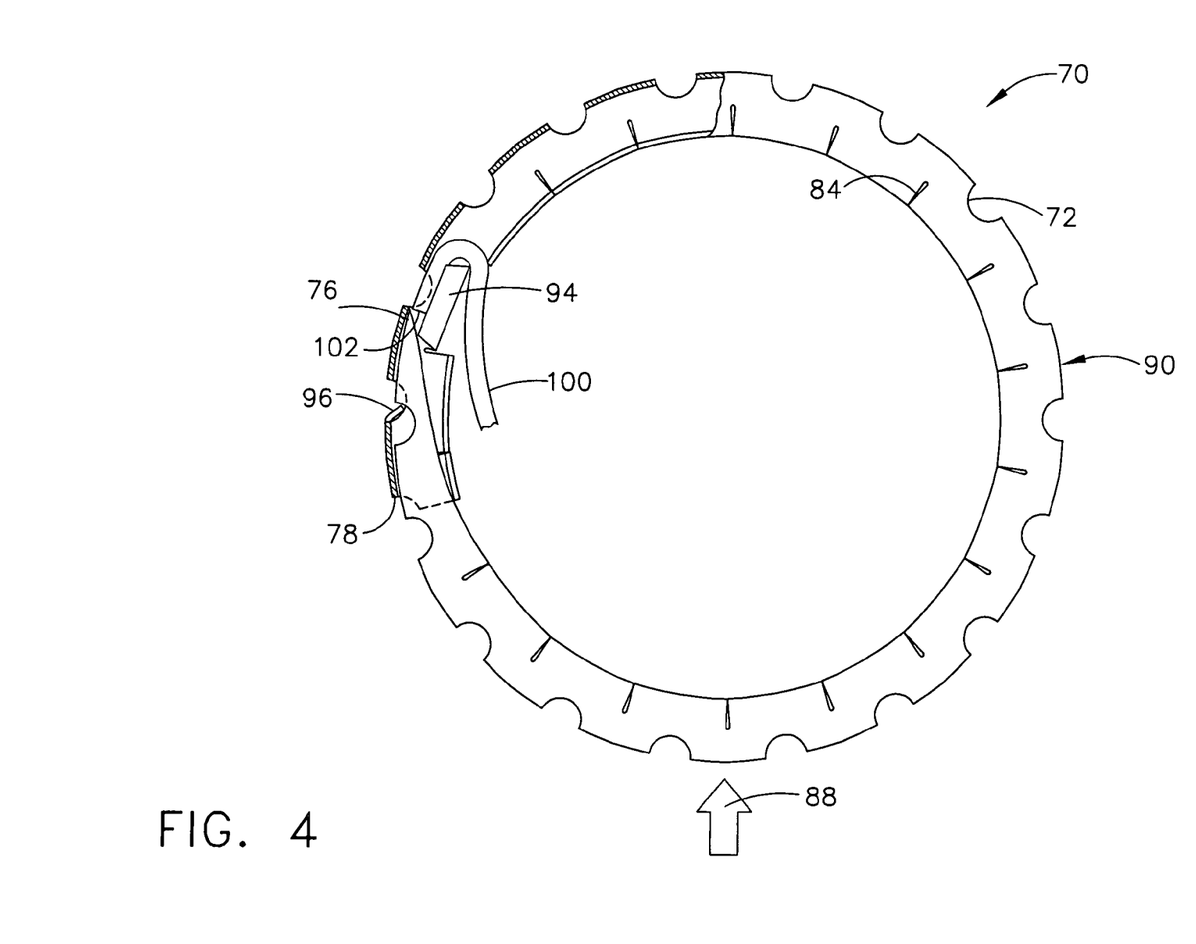
FIG. 4 is another side elevation of FIG. 2, showing the needle collapsed to form a closed circular anchor.

FIGS. 2-4 illustrate an arcuate, generally C-shaped suturing needle 70 according to one embodiment of the present invention. Needle 70 is shown in the form of a generally curved hollow tube having a generally circular cross-section which has equally spaced apertures 72 through an outer circumference 74 thereof. Needle 70 has a point end 76 and a rear end 78 spaced apart by a gap 80. Apertures 72 can have the same pitch as teeth 34 and 44, such that drive and driven sprockets 30 and 40 both engage apertures 72 of needle 70 to cause it to rotate within track 6. Two sprockets engage needle 70 so that one sprocket is always engaged when arcuate gap 80 passes the other sprocket. Accordingly, the spacing of sprockets 30 and 40 can be greater than gap 80. Gap 80 can be about 60 degrees of needle circumference, or in one embodiment, about 0.25 inches. Needle 70 can have an outside diameter of about 0.50 inches.

FIG. 3 shows needle 70 having an inner circumference 82. About inner circumference 82 are substantially equal spaced notches 84 which extend generally radially outwardly. Notches 84 can be spaced between apertures 72 in a staggered manner to provide a substantually uniform bending stiffness along needle 70. Needle 70 can be formed to have an overall bending stiffness which enables it to penetrate body tissue under tangential force 86 with minimal deflection, but when desired can be permanently deformed to a closed circle 90 when a radial forces 88 is applied, as shown in FIG. 4. Notches 84 can be sized and shaped such that they become substantially closed as needle 70 is deformed to a closed circle 90. Some notches 84 can become closed prior to other notches 84 being closed. In one embodiment, the notches 84 can close in a generally one-at-a-time, sequential fashion, such as wherein when one notch is closed, stiffness at that point in the needle increases and adjacent notches successively close. The needle curvature, needle material, thickness of its tubular wall, size and spacing of notches can be varied as desired to provide a desired overall stiffness of needle 70. When a needle is deformed to a closed circle 90, it forms a suture anchor, as hereinafter described.

In one embodiment, needle 70 can have a generally tubular cross-section about 0.032 inches in diameter and be formed of a series 300 stainless steel sheet material having a thickness of about 0.002 inches. The sheet material can be wrapped, rolled, or otherwise formed to provide a tube with butted edges 92 at the inner circumference 82, as best seen in FIG. 2. In the embodiment shown, the butted edges 92 are not welded or otherwise attached. Apertures 72 and notches 84 can be formed in needle 70 by a wire EDM process. Notches 84 can be about 0.001 to about 0.010 inches wide and have a depth of about 0.010 to about 0.020 inch. In one embodiment, notches 84 are about 0.002 inch wide and have a depth of about 0.016 inch. For needle assembly to suturing mechanism 2, needle 70 may be twisted slightly to form a spiral shape in order to progressively feed it into track 6, without permanently deforming needle 70.

FIG. 3 shows needle 70 having a length of about one inch of suturing material 100 within its hollow tubular body. Material 100 can be, for instance, a 0.005 inch diameter polypropylene monofilament or a woven strand folded back on itself one or more times. Material 100 can include a lead end 102 and a tail end 104 and a fold 106. Lead end 102 can be crimped to needle 70 by a bent flap 94 of needle 70 after material 100 has been inserted into needle 70. Needle 70 can include another tab 96 bent inward about 45 degrees toward needle point 76 and near rear end 78. Tab 96 can be sized and shaped to capture an aperture 72 (such as the aperture closest to needle point 76 as shown in FIG. 4) to prevent needle point 76 retracting from rear end 78 when needle 70 is collapsed to closed circle 90.

Tail end 104 can be associated with a slidable button anchor 110, with button anchor 110 slid over tail end 104 and a knot 108 tied in tail end 104 just outside slidable anchor 110. Knot 108 holds anchor 110 against rear end 78 of needle 70 as needle 70 slides within track 6 of housing 4. Anchor 110 can be shaped to enable it to pass through track 6 with needle 70. Anchor 110 can be formed of a series 300 stainless steel with a thickness of about 0.03 inches. Anchor 110 can include a hole 112 through which suture material 100 passes. Hole 112 can be configured to provide one way movement of suturing material 100. For instance, hole 112 can be configured to provide a tight fit about suturing material 100, or alternatively, hole 112 can include a taper inward to a sharp edge 114 at a side 116 of anchor 110 so that material 100 can slide through anchor 110 in only one direction, toward side 116 from the opposite side of anchor 110. This enables anchor 110 to gather pleats of body tissue, as described herinafter.

Housing 4 can be provided with openings extending into track 6 through which several of teeth 34 and 44 of sprockets 30 and 40 extend to engage apertures 72 of needle 70. Housing 4 also has an outer end surface 26 and a radially extending opening 29 extending from end 26 to needle track 6. Opening 29 can have a rectangular (or other non-circular) shape to serve as a guide for a plunger 120 having a shaft with rectangular (or other non-circular) cross-section, to prevent plunger 120 from rotating in hole 29. Alternatively, hole 29 can be circular with a keyway, and plunger 120 can have a round shaft with key protruding into a keyway.

Plunger 120 can include a first end 122 and a second T-shaped end 124. First end 122 can include a concave groove shaped similar to needle track 6, such that when plunger 120 is in its retracted position, end 122 can be aligned with and serve as a portion of track 6. T-shaped end 124 can be connected to a cable 118, which can be pulled to actuate plunger 120 from its retracted position to where it applies a radial force to close needle 70, as hereinafter described. Plunger 120 can be formed of a series 300 stainless steel. In one embodiment, plunger 120 can be supported to move approximately 0.25 inch from retracted position to an extended position by stainless steel pull cable 118. Pull cable 118 can be about 0.012 inches in diameter and can comprise a conventional woven wire cable intended for tensile loading. For load balancing, cable 118 can include a forked or split wire portion so as to be attached two either end of the T-shaped end 124, with the split halves of pull cable 118 routed along opposite sides of housing 4 as shown in FIG. 1.

Housing 4 can include an annular recess at end 26, the recess centered about hole 29. The annular recess can house compression spring 126. Compression spring 126 can be disposed about plunger 120 to bias plunger 120 in a retracted position when pull cable 118 is not pulled. If desired, a portion of the T-shaped end 124 can act as a stop (such as by abutting against a portion of housing end 26) when cable 118 is pulled, so that needle 70 is not deformed further than desired to form closed circle 90.

FIG. 4 shows needle 70 deformed to form closed circle 90. Pointed end 76 is shown disposed in the end 78 of tubular needle 70. The wall thickness of the material from which tubular needle 70 is formed can be selected such that the tubular needle 70 is flexible enough to allow flairing of the edges 92 near end 78, so as to accomodate the tapered outer surface of pointed end 76. Accordingly, pointed end 76 is nested within end 78, and body tissue is protected from further contact with pointed end 78. The lead end 102 of suture material 100 remains crimped to needle 70 just beyond the nested pointed end 78, and closed circle 90, still connected to suture material 100, forms an anchor at lead end 102 of suture material 100.

Figure 5:
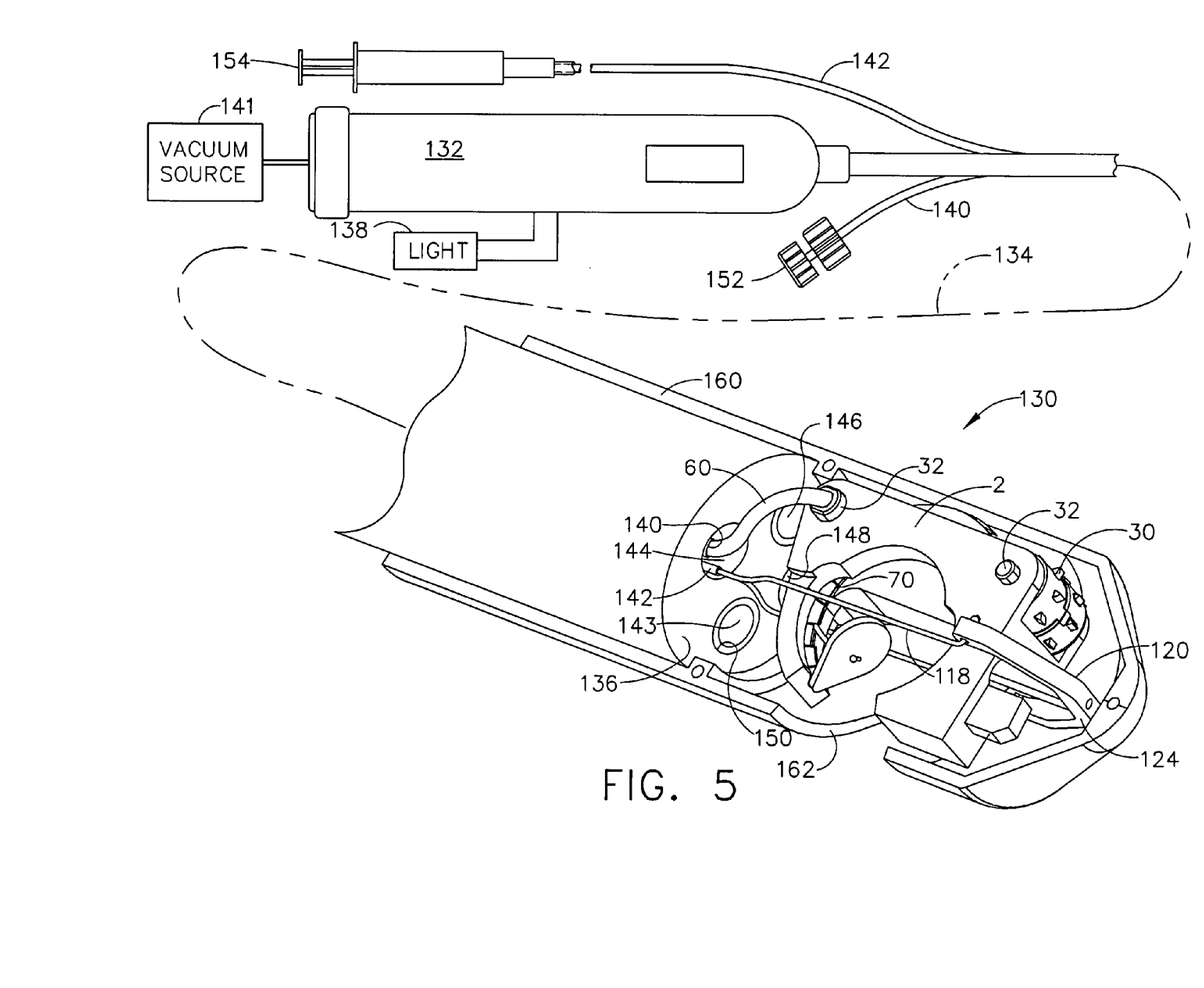
FIG. 5 is a perspective view of an endoscope showing control of an attached suturing mechanism.

With reference to FIGS. 5-13, and endoscope 130 is shown fitted with suturing mechanism 2, and a method of using endoscope 130 is illustrated. FIG. 5 shows endoscope 130 having a handle 132, a flexible body 134 with a distal end 136, a light 138, a twist cable sheath 140, a vacuum source 141, a pull cable sheath 142, camera 143, and a transparent shroud 160. Flexible body 134 can include four separate passageways therethrough. At distal end 136 is seen a first passageway 144, which is a working channel; a second pasageway 146, a third passageway 148, and a fourth passageway 150. Twist cable sheath 140 can extend from a position adjacent to handle 132 and extend through first passageway 144 of flexible body 134 to distal end 136 where it terminates. A twist cable 60 fixedly connected to axle 32 of drive sprocket 30 can extend through sheath 140 to a twist handle 152. Twist handle 152 can be removably connected to cable 60 for manually operating drive sprocket 30 of suturing mechanism 2.

Pull cable sheath 142 can extends from a position adjacent to handle 132 through first passageway 144 of flexible body 134 along side sheath 140 to distal end 136 where it terminates. Pull cable 118 can extend through sheath 142 to a pull handle 154. Pull handle 154 can be removably connected to cable 118 for manually operating plunger 120 of suturing mechanism 2. Light can be transmitted from light 138 by one or more optical fibers which extend through second and third passageways 146 and 148. Camera 143 can be positioned at the distal end 136 and can be operatively connected to wiring extending from handle 132 through fourth passageway 150. A vacuum source 141 can provide vacuum at the distal end 136, such as by communicating through one or more passages in the endoscope. For instance, vacuum source 142 can be in flow communication with first passageway 144.

Endoscope 130 can have a length of at least about 40 inches and a diameter of about 0.55 inches. Transparent shroud 160 can be formed of clear polycarbonate and can have an outside diameter of about 0.75 inches and a length of about 2 inches. Shroud 160 can be adapted to be releasably attachable to the end of endoscope 130, such as by press-fit to prevent the shroud from rotating with respect to the endoscope. Alternatively, a snug silicone rubber washer between the shroud and endoscope can be employed. Shroud 160 has an opening 162 located near open end 12 of track 6 of suturing mechanism 2. When vacuum source 141 is activated, suction occurs at opening 162 to enable a pleat of body tissue to be pulled into the path of needle 70 for suturing.

Opening 162 can be about 0.25 inches wide (as measured parallel to the longitudinal axis of the endoscope) and opening 162 can extends about 120 degrees around the circumference of shroud 160. Shroud 160 can be formed of a transparent material so that light 138 illuminates the area of the body to be sutured and camera 143 transmits that view to the operator of the endoscope.

Figure 6:
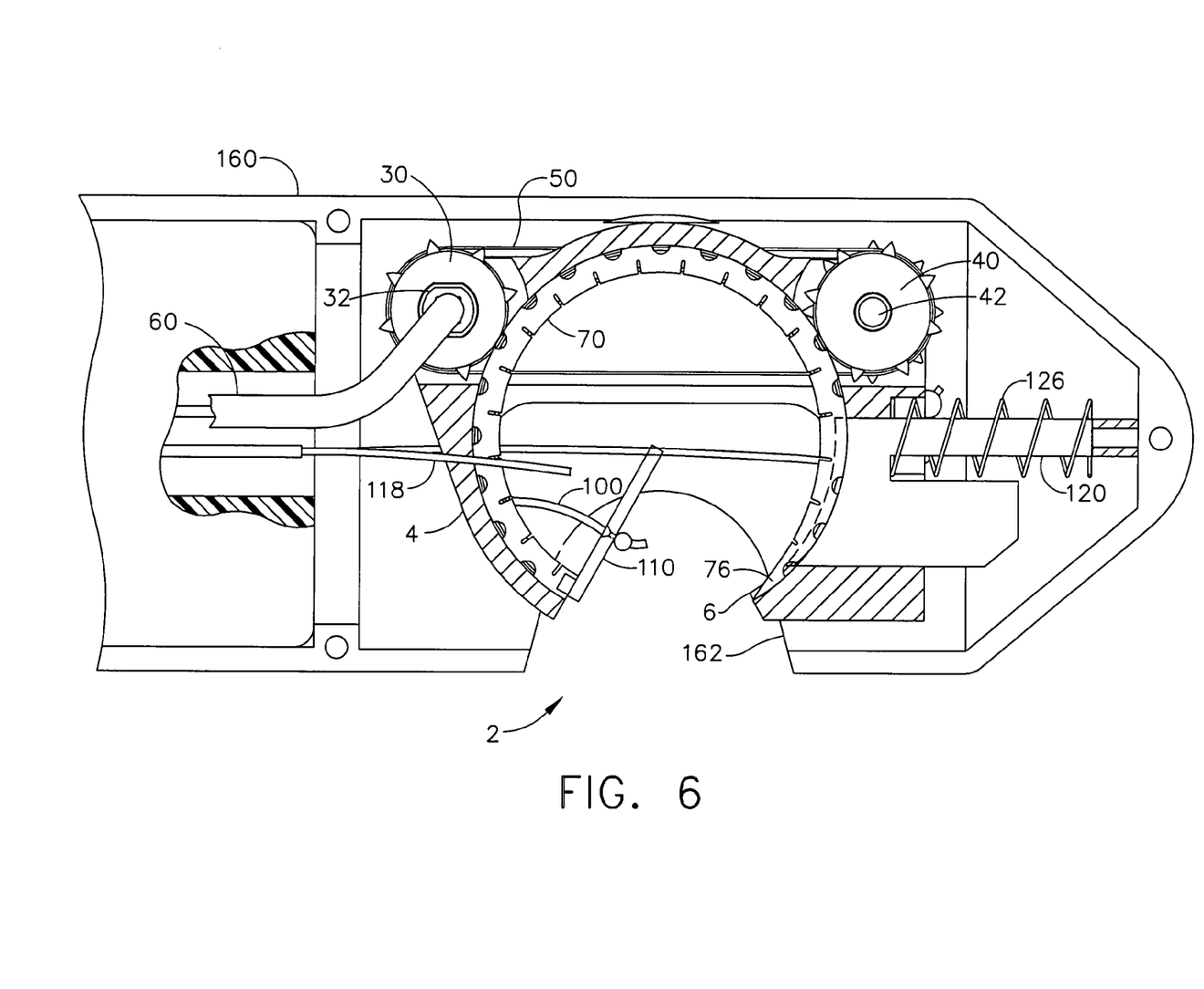
FIG. 6 is a cross-sectioned elevation view of a suturing mechanism removably attached to an endoscope by means of a transparent shroud.

FIG. 6 shows a cross-sectioned view of shroud 160 and suturing mechanism 2. This view shows needle 70 in track 6 engaged by sprockets 30 and 40 to rotate the needle past opening 162 in shroud 160. Mechanism 2 can be supported by shroud 160 at sprocket shafts 32 and 42. For instance shafts 32 and 42 can be supported in journals formed in shroud 160. Plunger 120 is shown in its retracted position, abutting an internal surface of a distal nose of shroud 160.

Figure 7:
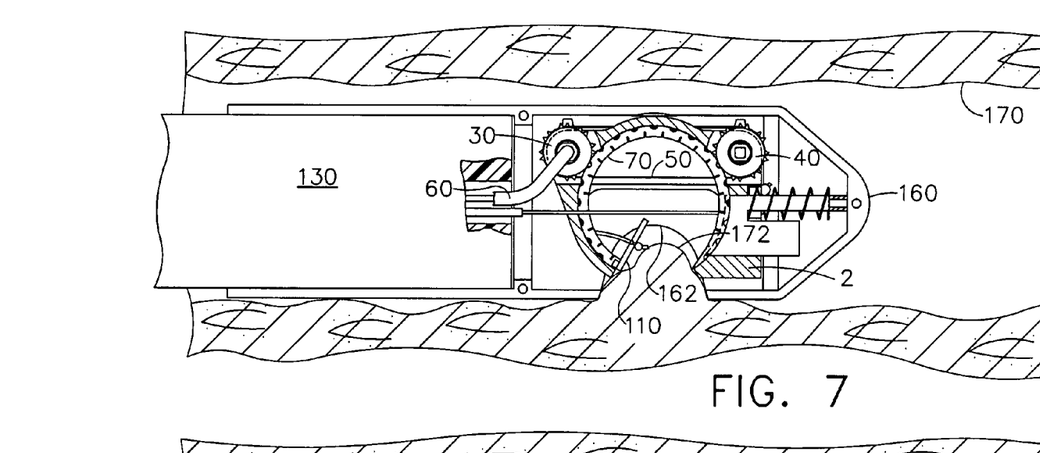
FIG. 7 is a cross-sectioned elevation view of a first step in a suturing method showing penetration of a pleated portion of body tissue by the needle, leaving an anchor button at entrance to needle hole.

FIGS. 7-13 show a method of suturing body tissue in a human alimentary canal 170 using endoscope 130 and suturing mechanism 2. FIG. 7 shows a first step of sucking a first pleat 172 of body tissue into opening 162.

Figure 8:
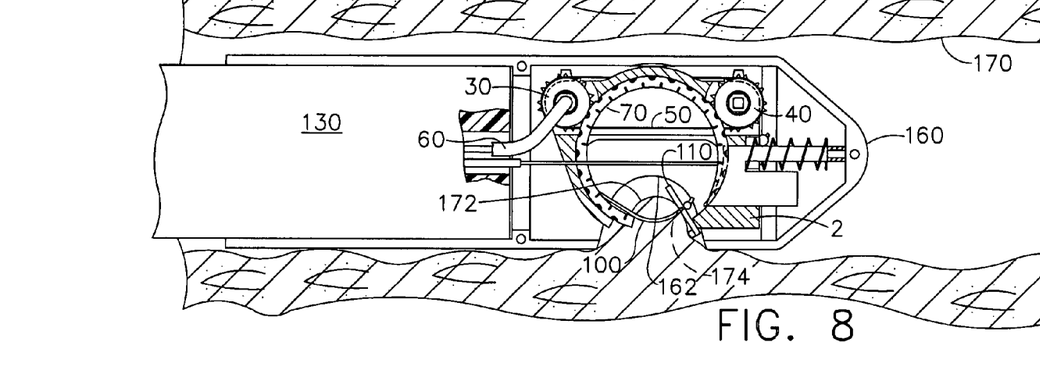
FIG. 8 is a cross-sectioned elevation view of a second step in a suturing method showing suturing material drawn through a first pleat.

FIG. 8 shows a second step of actuating twist cable 60 to drive needle 70 almost a 360 degree rotation through pleat 172, leaving anchor button 110 at an entrance point 174 of pleat 172, while suturing material 100 is shown partially withdrawn from needle 70.

Figure 9:
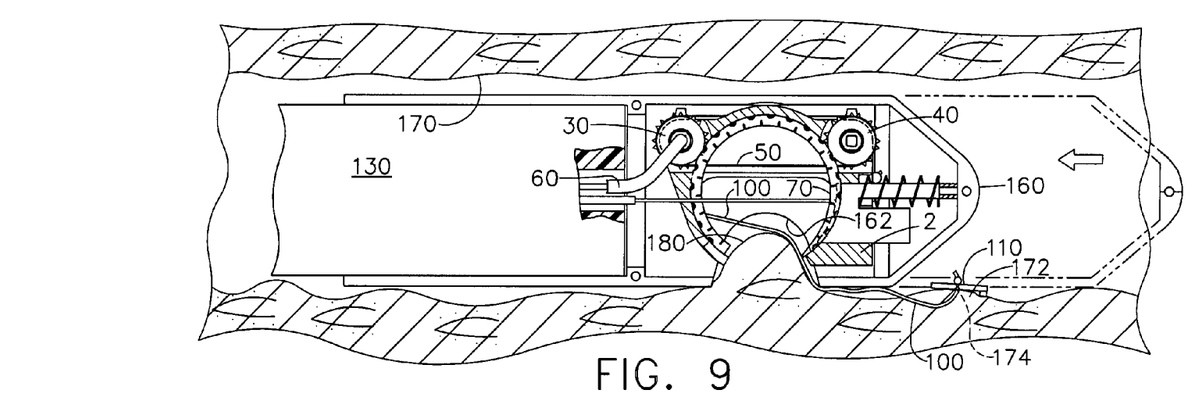
FIG. 9 is a cross-sectioned elevation view of a third step in a suturing method showing sucking a second pleat into the suturing mechanism.

FIG. 9 shows a third step of moving endoscope 130 to an adjacent area of alimentary canal 170, where a second pleat 180 is sucked into opening 162 for initiating a second suture. Anchor 110 remains at point 174 of first sutured pleat 172, and suture material 100 is shown further withdrawn from needle 70.

Figure 10:
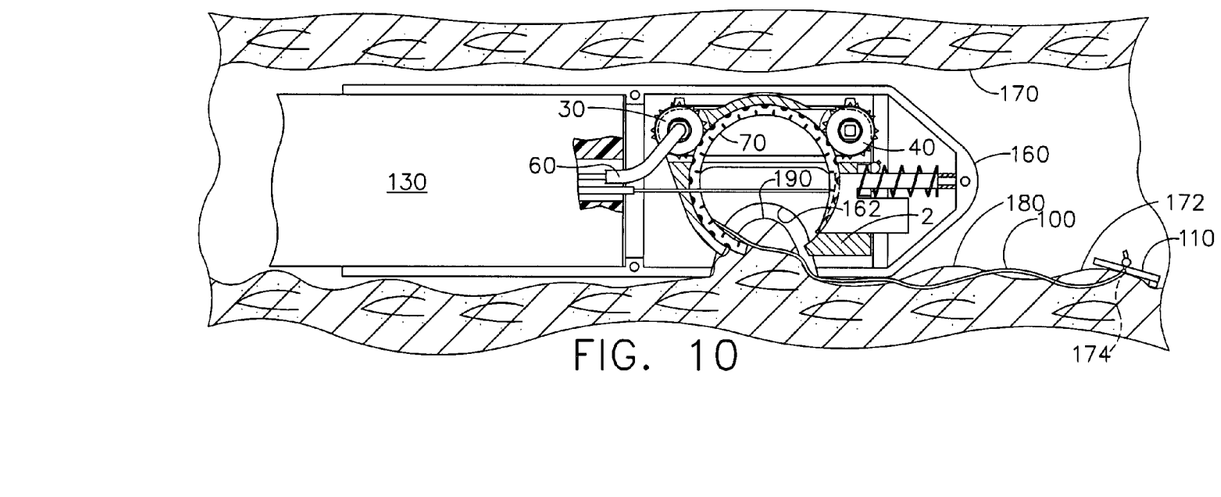
FIG. 10 is a cross-sectioned elevation view of another step in a suturing method showing completing the suturing of a third pleat.

FIG. 10 shows another step of the suturing method in which a third pleat 190 of body tissue is sucked into opening 162, after which needle 70 is rotated third about track 6 to pull suturing material 100 through third pleat 190.

Figure 11:
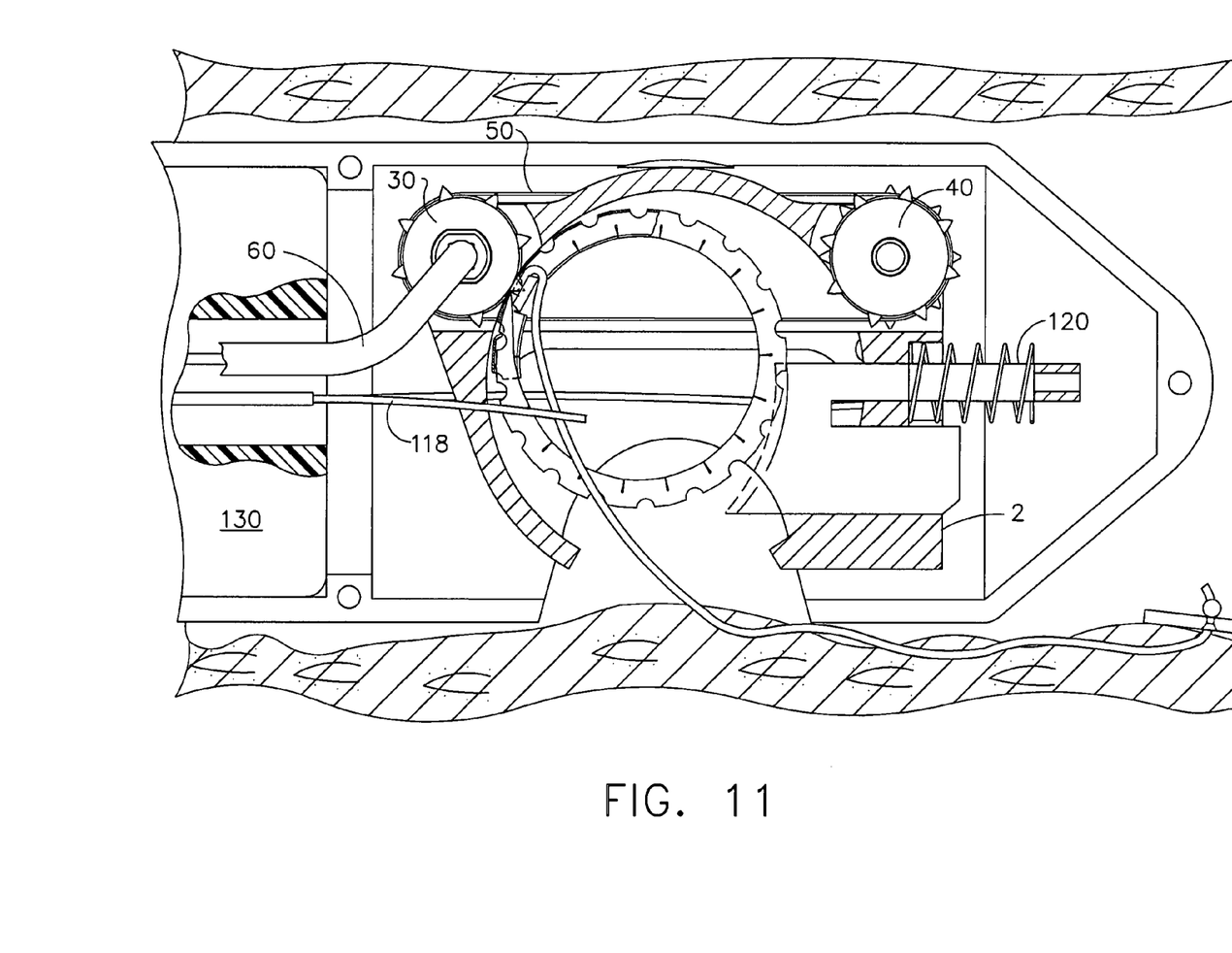
FIG. 11 is a cross-sectioned elevation view of another step in a suturing method showing deformation of the circular needle to form another anchor.

FIG. 11 shows another step in which plunger 120 is actuated by pulling cable 118 to move plunger 120 to close needle 70 on itself to form closed circle 90. In the process of closing the notches 84 of needle 70, suturing material 100 can be pinched in the notch it had been withdrawn from. As a result no further material 100 can be withdrawn, and closed circle 90 becomes an anchor at one end of the suturing material 100. Needle 70 may be collapsed regardless of its rotational position within needle track 6. Therefore, it may be collapsed while still engaging tissue or after it has passed through tissue. In these FIGURES, closed circle 90 is shown formed outside of the body tissue. Alternatively, the needle 70 can be closed with the needle still engaging tissue, at the surgeon's discretion.

Figure 12:
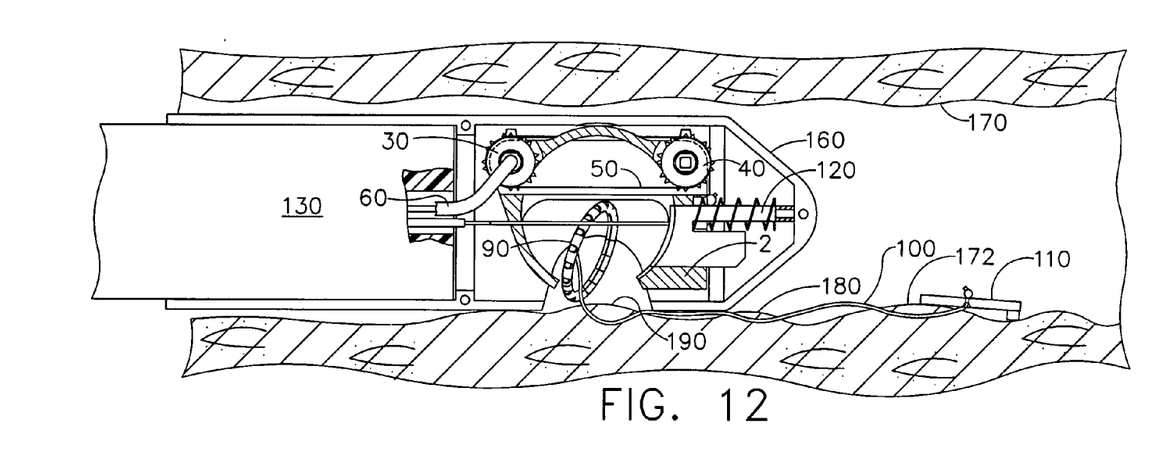
FIG. 12 is a cross-sectioned elevation view of another step of a suturing method showing terminating the suture of multiple pleats with the closed needle.

FIG. 12 shows another step of the suturing method in which the plunger is retracted. Once needle 70 is closed on itself to form needle circle 90, its size is reduced enough that needle circle 90 will drop out of open end 12 of track 6 and opening 162 of shroud 160. Closed circle 90 can be about 0.25 inches in diameter. It may also be discharged laterally from suturing mechanism 2. When pull cable 118 is released, spring 126 returns plunger 120 to its reset position.

Figure 13:
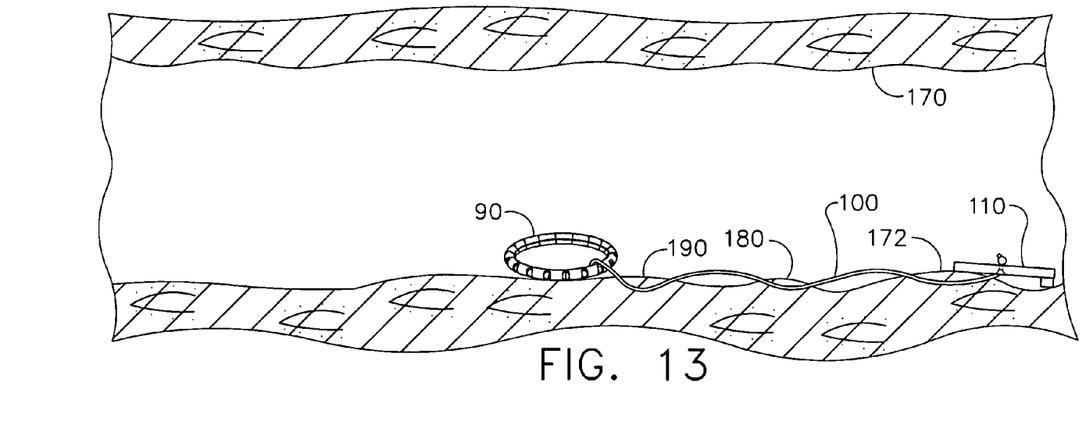
FIG. 13 is a cross-sectioned elevation view of another step in a suturing method showing removing the endoscope.

FIG. 13 shows endoscope 130 removed from alimentary canal 170 and closed circle 90 at one end of suturing material 100, and anchor button 110 at the other end, and suturing material 100 passing loosely through three pleats 172, 180 and 190, which tend to flatten and cause knot 108 to face inward within alimentary canal 170.

Figure 14:
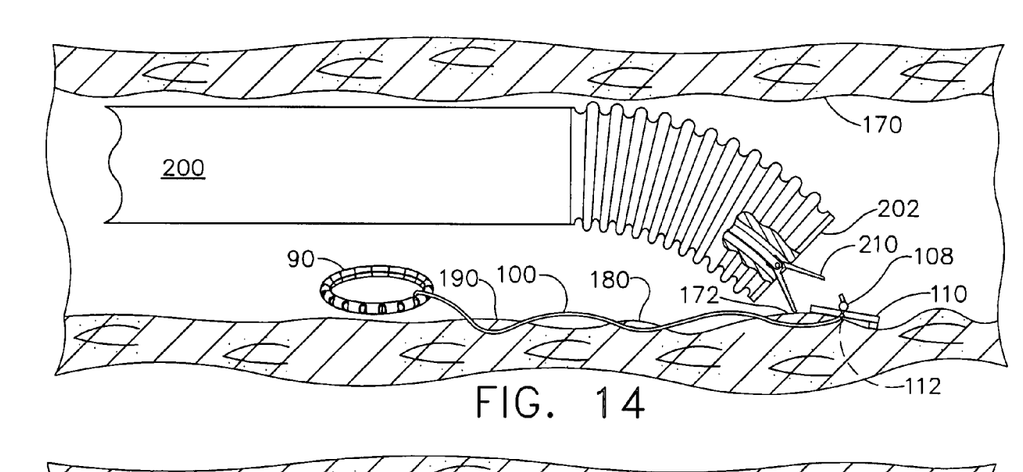
FIG. 14 is an illustration of a second endoscope being advanced in the GI tract.

FIG. 14 shows a final step of gathering three pleats by introducing a second endoscope 200, which has distal end 202 and conventional grippers 210. Grippers 210 are connected to an operating handle by one or more pull wires or cables. Grippers 210 can be actuated to grip knot 108 in tail end 104 of suturing material 100, and retract knot 108 through a channel in endoscope 200 while anchor button 110 is held in place by distal end 202 of endoscope 200. To prevent anchor button 110 from entering the channel in endoscope 200, anchor button 110 can be sized to prevent button 110 from passing through the channel through which grippers 210 operate. When knot 108 and anchor button 110 are released, anchor button remains in position with the pleats gathered due to a tight fit between hole 112 of anchor button 110 and suturing material 100. Alternatively, a sharp edge 114 at a side 116 of anchor button 110 engages material 100 and thereby prevents reverse movement of material 100 through button 110.

Figure 16:
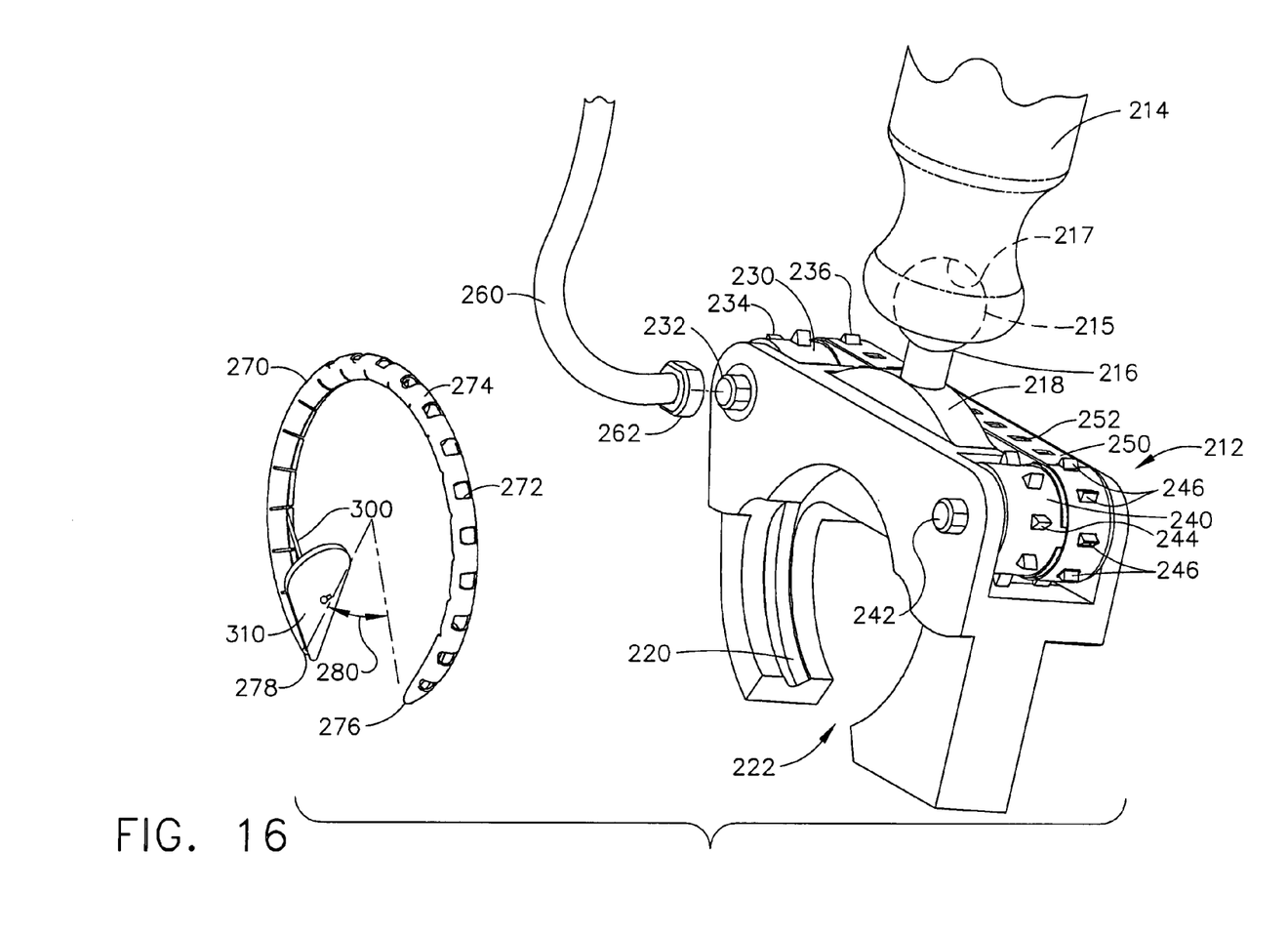
FIG. 16 is a perspective view of a suturing mechanism shown attached to a handle via a flexible joint.

Referring now to FIG. 16, there is shown a suturing mechanism 212 attached to a handle 214 by a swivel joint 216. Hand operation of a suturing mechanism on the end of a handle allows a surgeon to controllably place an arcuate needle into body tissue. The surgeon may also drive the needle backwards so that if it is partially penetrated into tissue, it can be withdrawn and repositioned in the tissue if so desired. Handle 214 can be formed of a rigid medical grade plastic or 300 series stainless steel. Swivel joint 216 is made from surgical grade stainless steel.

Suturing mechanism 212 has a housing 218, a drive sprocket 230, a driven sprocket 240, a drive belt 250, a twistable flexible cable drive 260, a malleable C-shaped needle 270, suturing material 300, and a slidable suture material anchor 310. Suturing mechanism 212 is similar to suturing mechanism 2, except that there is no needle closing plunger 120 and no vacuum source 141 to lift tissue into the path of needle 270. C-shaped needle 270 is similar to needle 70 except that a point end 276 and a rear end 278 are spaced apart by a larger gap 280, as explained hereinafter. The size of suturing mechanism 212 is not as constrained when attached to handle 214 as suturing mechanism 2 is when used with endoscope 130.

In FIG. 16, housing 218 has a arcuate groove therein, forming a needle track 220. Track 220 is sized to hold C-shaped needle 270, similar to track 6 holding needle 70. Housing 218 has an open end 222 in track 220, similar to open end 12 in track 6, which provides clearance for tissue to enter the path of needle 270. Housing 218 can be formed of a series 300 stainless steel via machining processes commonly known in the fabrication art, such as casting, turning, milling, and electro-discharge machining (EDM).

Housing 218 can be about 0.74 inches long, about 0.25 inches wide, and about 0.55 inches high. Needle track 220 can be about 0.50 inches in diameter at its root and can have a groove depth of about 0.016 inches. Open end 222 can be about 0.25 inches wide. Sprocket 230 can have an axle 232 splined and/or press-fit therethrough, and sprocket 240 can have an axle 242 splined and/or press-fit therethrough. Axles 232 and 242 can be substantially parallel to each other.

Drive sprocket 230 can have a first set of equally spaced teeth 234 and a second adjacent set of equally spaced teeth 236 extending about its circumference. Driven sprocket 240 can have a first set of equally spaced teeth 244 and a second adjacent set of equally spaced teeth 246 extending about its circumference. Teeth 234 and 244 can have a common pitch, and teeth 236 and 246 can also have a common pitch, which may or may not be different from the pitch of teeth 234 and 244. Sprockets 230 and 240 may be single parts or two components keyed together for ease of forming individual rows of teeth. Sprockets 230 and 240 can be formed of series 300 stainless steel and teeth 234, 236, 244, and 246 can be formed by a wire EDM process. Each sprocket can be about 0.15 inches diameter at the root of the teeth. Axles 232 and 242 can be formed of series 300 stainless steel and can be about 0.077 inches in diameter and about 0.325 inches long.

Drive belt 250 can be a continuous belt extending around sprockets 230 and 240. Drive belt 250 can include apertures 252 equally spaced along the length thereof. Apertures 252 can have the same pitch as teeth 236 and 246 so that when drive sprocket 230 is rotated, drive belt 250 positively rotates driven sprocket 240 the same amount. Drive belt 250 can be formed of series 300 stainless steel, and can have a thickness of about 0.002 inches, a width of about 0.072 inches, and a length of about 1.65 inches.

FIG. 16 shows twistable flexible cable 260 positioned for engagement with axle 232 of drive sprocket 230. Cable 260 can include a collar 262, which can be removably attached to axle 232 for assembly purposes, but is rotationally fixed thereto when assembled, such as by pin, spline or press-fit, so that when cable 260 is twisted, axle 232 rotates, causing sprocket 230 to rotate, thereby driving belt 250 to rotate sprocket 240 in the same direction and speed as sprocket 230. Cable 260 can have a diameter of about 0.09 inches, and can be formed of series 300 stainless steel wire similar to a speedometer cable, low in bending stiffness but relatively high in twisting stiffness. Lubrication of rotating and sliding stainless steel parts in housing 218 can be accomplished with any suitable lubricant, including without limitation teflon coating, soap, or Vaseline brand materials.

Figure 15:
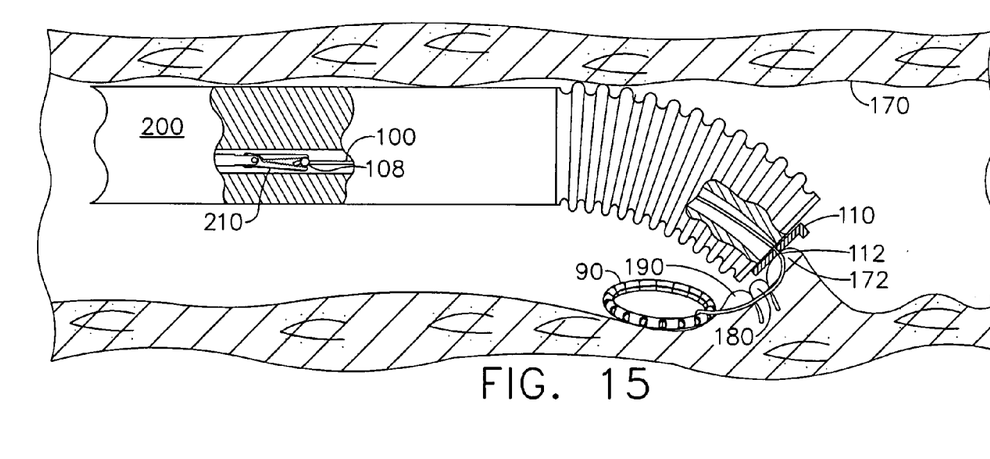
FIG. 15 is a cross-sectioned elevation view of a final step in a suturing method showing the second endoscope gathering the sutured pleats by pulling a knotted end of the suture through a tight fitting hole in the button anchor.

FIG. 15 also shows C-shaped suturing needle 270. Needle 270 can be in the form of a curved hollow tubular structure having a generally circular cross-section which has equally spaced apertures 272 through an outer circumference 274 thereof. Needle 270 has a pointed end 276 and an opposite second end 278 spaced apart from pointed end 276 by a gap 280. Apertures 272 can have the same pitch as teeth 234 and 244, such that drive and driven sprockets 230 and 240 both engage apertures 272 of needle 270 to cause it to rotate within track 220. Two sprockets engage needle 270 so that one sprocket is always engaged when gap 280 passes the other sprocket. The angular spacing of sprockets 230 and 240 along the track 220 is greater than gap 280. Gap 280 can be about 60 degrees of needle circumference, or about 0.25 inches. Needle 270 can be about 0.50 inches in outside diameter.

Housing 218 has swivel joint 216 fixedly attached thereto. Swivel joint 216 has a spherical or semi-spherical or cylindrical surface 215, as commonly known in the art, with correspondingly shaped mating surface 217 engaging surface 215 to enable sliding between them, preferably with adjustable friction, to enable a rotational position to be maintained once it is established. Swivel joint 216 is also fixedly attached to handle 214 such that suturing mechanism 212 is rotatable relative to handle 214. Rotation is achieved either manually before contact with body tissue or by pressing suturing mechanism 212 against body tissue while manually twisting and/or tilting handle 214. Alternatively, a joystick or other suitable mechanism can be associated with handle 214 to vary the orientation of the suturing mechanism relative to the handle 214.

Cable 260 can be routed through swivel joint 21 and into handle 214, if desired, or can be routed alongside handle 214 as shown in FIG. 16. Operation of suturing mechanism 212 is similar to that of suturing mechanism 2 in steps illustrated in FIGS. 8-10, except that no vacuum is used. Instead of vacuum to lift tissue into open end 222, a surgeon may manually lift tissue into open end 222, or alternatively, open end 222 of housing 218 can be pressed against body tissue to position tissue within the path of needle 270. Cable 260 can be twisted manually while handle 214 is held by the surgeon to position needle 270.

Figure 17:
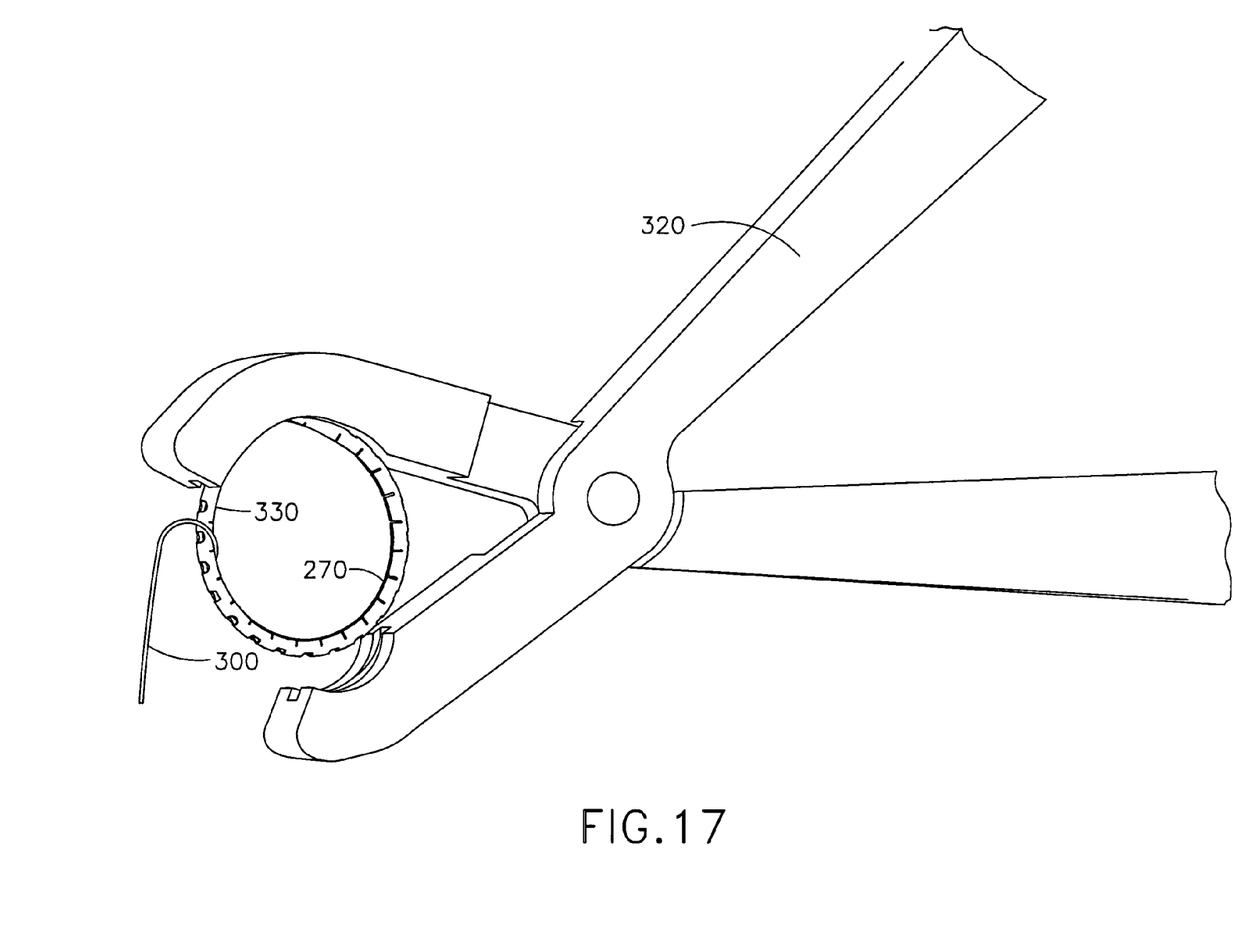
FIG. 17 is a perspective view of a pliers mechanism for forming a C-shaped suturing needle to a closed circular anchor.

Needle 270 is similar in construction to needle 70. However, because it is intended for use outside the alimentary canal, where access to suturing material is readily available, a length of suturing material 100 may or may not be contained within needle 270. Also, needle 270 may or may not be collapsed to form a closed circle. Instead, the needle may be removed and the suturing material may be tied off manually. In one embodiment, needle 270 is similar to needle 70 and is intended to be closed to form an anchor. In this embodiment, needle 270 has notches extending radially outward from its inner circumference similar to needle 70, which allow needle 270 to be collapsed. However, instead of plunger 120 in suturing mechanism 2, a separate manually operated pliers 320, as shown in FIG. 17, may be used to form needle 270 to a closed circle 330 after needle 270 is removed from suturing mechanism 212. Uncollapsed needle 270 may be "sprung" or otherwise slightly deformed by the surgeon to remove it from track 220 of suturing mechanism 212.

In another embodiment, needle 270 can have a length of about one inch of suturing material 300 within its hollow tubing body. Material 300 can be about 0.005 inch diameter polypropylene monofilament or a woven strand folded back on itself one or more times. Material 300 can include a lead end connected to needle 270 similar to material 100 folded and connected to needle 70. Material 300 can include a tail end onto which a slidable button anchor 310 is positioned, with a knot tied in the tail end just outside slidable anchor 310, similar to anchor button 110 and material 100 with knot 108. Anchor 310 can be shaped to enable it to pass around track 220 with needle 270. Anchor 310 can be formed of series 300 stainless steel with a thickness of about 0.03 inches. Anchor 310 can include a hole adapted to permit generally one way passage of suture material 300.

While the present invention has been illustrated by description of several embodiments, it is not the intention of the applicant to restrict or limit the spirit and scope of the appended claims to such detail. Numerous other variations, changes, and substitutions will occur to those skilled in the art without departing from the scope of the invention. Moreover, the structure of each element associated with the present invention can be alternatively described as a means for providing the function performed by the element. It will be understood that the foregoing description is provided by way of example, and that other modifications may occur to those skilled in the art without departing from the scope and spirit of the appended Claims.

What is claimed:

1. A needle for use in suturing, the needle formed as a single-piece body and having a freestanding, generally curved first configuration extending through an arc of at least about 180 degrees, wherein the needle is configured to pierce and pass through tissue, wherein the needle is deformable at a plurality of predetermined positions spaced apart along the arc of the needle, and wherein the needle is deformable from the first configuration to a second configuration; and the needle comprising a pointed first end and an open second end, wherein the pointed first end is received within the open second end upon deformation of the needle from the first configuration to the second configuration.

2. The needle of claim 1 wherein the needle extends through an arc of at least about 270 degrees.

3. The needle of claim 1 wherein the needle is deformable from a first open configuration to a second closed configuration.

4. The needle of claim 1 wherein the needle comprises a plurality of sequentially deformable segments.

5. The needle of claim 1 comprising a plurality of circumferentially spaced apart notches extending from an inner circumferential portion of the needle.

6. The needle of claim 1 comprising a plurality of notches sized such that the notches are closed as the needle is deformed from the first configuration to the second configuration.

7. A needle for use in suturing, the needle formed as a single-piece body and comprising a generally curved tubular portion, wherein the generally curved tubular portion extends through an arc of at least about 180 degrees, wherein the needle is configured to pierce and pass through tissue, wherein the needle is deformable at spaced apart, predetermined locations along the length of the unitary, generally curved tubular portion from a first generally open configuration to a second generally closed configuration; and the needle comprising a pointed first end and an open second end, wherein the pointed first end is received within the open second end upon deformation of the needle from the first generally open configuration to the second generally closed configuration.

8. The needle of claim 7 wherein the unitary, generally curved tubular portion extends through an arc of at least about 270 degrees.

9. The needle of claim 7 comprising a length of suture material disposed within the tubular portion of the needle.

10. The needle of claim 7 wherein the open second end communicates with an internal space within the tubular portion.

11. The needle of claim 7 wherein the needle is deformable from an open configuration to a closed configuration.

12. A method of suturing comprising the steps of:
providing a needle formed as a single-piece body, the needle being deformable from a first configuration to a second configuration;
providing suture material associated with the needle;
piercing tissue with the needle;
passing the needle at least one time through the pierced tissue; and
deforming the needle from the first configuration to the second configuration;
wherein the needle comprises a pointed first end and an open second end, and the pointed first end is received within the open second end upon deformation of the needle from the first configuration to the second configuration.

13. The method of claim 12 wherein the step of deforming comprises deforming the needle from an open configuration to a closed configuration.

14. The method of claim 12 comprising passing the needle through tissue multiple times.

15. The method of claim 12 comprising passing the needle through multiple tissue sites, and further comprising the step of gathering the multiple tissue sites by pulling the suture material after the step of passing the needle through the multiple sites.

16. A medical apparatus for suturing comprising:
a generally arcuate needle formed as a single-piece body, wherein the needle is configured to pierce and pass through tissue, wherein the needle is deformable from a first configuration to a second configuration;
the needle comprising a pointed first end and an open second end, wherein the pointed first end is received within the open second end upon deformation of the needle from the first generally open configuration to the second generally closed configuration; and
a needle drive assembly for receiving the generally arcuate needle and driving the needle along a generally arcuate path, wherein the needle drive assembly comprises an element supported to move from a first position to a second position to deform the needle.

17. The medical device of claim 16 wherein the needle drive assembly comprises at least one rotatable element for driving the needle along the generally arcuate path.

18. The needle of claim 1, further comprising a suture secured to the needle, wherein the needle is deformable relative to the suture.

19. The needle of claim 1, wherein the second configuration forms a closed circle.

* * * * *